US00PP26033P3

(12) United States Plant Patent
Bradford

(10) Patent No.: US PP26,033 P3
(45) Date of Patent: Nov. 3, 2015

(54) INTERSPECIFIC TREE NAMED 'PLUMGIANT II'

(50) Latin Name: ***Prunus* sp.**
Varietal Denomination: Plumgiant II

(71) Applicant: Lowell Glen Bradford, Le Grand, CA (US)

(72) Inventor: Lowell Glen Bradford, Le Grand, CA (US)

( * ) Notice: Subject to any disclaimer, the term of this patent is extended or adjusted under 35 U.S.C. 154(b) by 164 days.

(21) Appl. No.: 13/998,857

(22) Filed: Dec. 16, 2013

(65) Prior Publication Data

US 2015/0173271 P1 Jun. 18, 2015

(51) Int. Cl.
*A01H 5/02* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

PP18,705 P2 4/2008 Bradford

*Primary Examiner* — Susan McCormick Ewoldt

(57) ABSTRACT

The present invention relates to an interspecific tree and more particularly to a new and distinct variety broadly characterized by a medium size, moderately vigorous, hardy, and very productive tree. Being self-unfruitful, the present variety requires cross pollination from an apricot, plum, or interspecific variety that blooms during the mid to late season, such as 'Blackred V' (U.S. Plant Pat. No. 19,576). The present variety produces a moderate amount of blossoms and pollen to entice strong bee activity to facilitate pollination. The fruit matures under the ecological conditions described in late July, with first picking on Jul. 27, 2013. The fruit is large in size, full black in skin color, orange yellow in flesh color, clingstone in type, oblate in shape, and very good in flavor.

1 Drawing Sheet

Botanical classification: *Prunus* sp.
Varietal denomination: 'PLUMGIANT II'.

BACKGROUND OF THE VARIETY

In a continuing effort to improve the quality of shipping fruits, I, the inventor, typically hybridize a large number of peach, nectarine, plum, apricot, and cherry seedlings each year. I also grow a smaller number of open pollinated seeds of each of these fruits. The present invention relates to a new and distinct variety of interspecific tree which has been denominated varietally as 'Plumgiant II'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2001 one such house containing three unpatented plum trees and two interspecific trees was crossed by me in this manner. To pollinate these trees I selected bouquets from several sources of apricot and interspecific plum-apricot hybrid trees without keeping specific written details. Upon reaching maturity the fruit from these trees was harvested and the seeds were removed, cracked, stratified and germinated as a group with the label "H8B". They were grown as seedlings on their own root in my greenhouse and upon reaching dormancy transplanted to a cultivated area of my experimental orchard located near Le Grand, Calif. in Merced County (San Joaquin Valley). During the summer of 2005 the claimed variety was selected by me as a single plant from the group of seedlings described above.

Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was true to type.

The present variety is most similar to 'Plumgiant I' plum tree (U.S. Plant Pat. No. 18,705) by being self-unfruitful and by producing fruit that is clingstone in type, entirely black in skin color, good in flavor, and that matures in the mid season, but is distinguished therefrom by producing fruit that is slightly smaller in size, that is oblate in shape instead of globose, that is orange yellow in flesh color instead of white, and that is less prone to internal browning.

SUMMARY OF VARIETY

The present interspecific variety is characterized by a medium size, moderately vigorous, hardy, and very productive tree. Being self-unfruitful, the present variety requires cross pollination from an apricot, plum, or interspecific variety that blooms during the mid to late season, such as 'Blackred V' (U.S. Plant Pat. No. 19,576). The present has a moderate amount of blossoms and pollen to entice strong bee activity to facilitate pollination. The fruit matures under the ecological conditions described in late July, with first picking on Jul. 27, 2013. The fruit is large in size, full black in skin color, orange yellow in flesh color, clingstone in type, oblate in shape, and very good in flavor.

DRAWING

The accompanying photograph consists of four whole fruits positioned to display the characteristics of the skin color and form, one fruit divided to reveal the flesh and stone, typical leaves, and two insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Aug. 3, 2013, on the original tree during its twelfth growing season. The flower and bud descriptions were developed during the previous blooming season. All major color code designations are by reference to the Inter-Society Color Council, National Bureau of Standards. Common color names are also used occasionally.

It is to be noted that the 2013 fruit season in California was very warm during the spring and the ripening times of almost all varieties were about ten days earlier than other years.

Parentage

Seed parent: Unknown.
Pollen parent: Unknown.

Tree

Size: Medium, reaching a height of 13' [3.96 m.] and a spread of 7' [2.13 m.] after twelve growing seasons utilizing typical pruning.

Vigor: Medium vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Central leader.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable mid to late seasonal blooming apricot, interspecific, or plum, such as 'Blackred V' interspecific tree (U.S. Plant Pat. No. 19,576).

Bearing: Regular bearer, with no crop failures observed.

Trunk:

- *Size*.—Medium, reaching a maximum diameter of 5" [127 mm.] after the twelfth growing season.
- *Texture*.—Medium shaggy.
- *Bark color*.—A Grayish brown [61. gy.Br] and Brownish gray [64. brGray] variegation with Moderate yellow brown [77. m.yBr] crevices present.
- *Lenticels*.—Approximate Number Per Square Inch: 4-6. Color: Strong yellowish brown [74. s.yBr]. Average Size: ⅛" [3.2 mm.]. Shape: Elongated, eye-shaped.

Branches:

- *Size*.—Diameter of main scaffold is 3½" [88.9 mm.] measured 12" above the crotch, diameter of secondary limb is 2¼" [57.2 mm.] measured 12" above the first fork.
- *Texture*.—Smooth on first and second year wood, increasing roughness with age.
- *Color*.—1st Year Wood: Grayish red [19. gy.R]. 2nd Year Wood: Moderate brown [58. m.Br]. Older Wood: A Grayish brown [61. gy.Br] and Brownish gray [64. brGy] variegation.
- *Lenticels*.—Number Per Square Inch: About 60 on second year wood. Color: Light yellowish brown [76. l.yBr]. Average Size: 1/64" [0.4 mm.]. Shape: Elongated, eye-shaped.

Leaves:

- *Size*.—Medium to small. Average Length: 3½" [88.9 mm.]. Average Width: 1 7/16" [36.5 mm.].
- *Arrangement*.—Alternate.
- *Thickness*.—Medium.
- *Form*.—Elliptical.
- *Apex*.—Acuminate.
- *Base*.—Acute with an average angle base angle of 70 degrees.
- *Surface*.—Smooth.
- *Color*.—Dorsal Surface: Moderate olive green [125. m.OlG]. Ventral Surface: Moderate yellow green [120. m.YG].
- *Margin*.—Finely serrate.
- *Venation*.—Pinnately net veined.
- *Petiole*.—Average Length: 9/16" [14.3 mm.]. Average Thickness: 1/16" [1.6 mm.]. Color: Light yellow green [119. l.YG] with Dark red [16. d.R] where exposed to sunlight.
- *Stipules*.—Number: Usually 2 per leaf, up to 6 per growing tip. Average Length: ¼" [6.4 mm.]. Color: Brilliant yellow green [116. brill.YG] becoming Light grayish reddish brown [45. l.gy.rBr] with age.
- *Glands*.—Number: Mostly 2 to 4 per leaf. Position: Alternately positioned on petiole and the leaf blade. Size: Small. Form: Globose. Color: Light yellow green [119. l.YG] acquiring a Moderate reddish brown [43. m.rBr] center with age.
- *Leaf buds*.—Pointed, medium.

Flower buds:

- *Hardiness*.—Hardy, with respect to central California winters.
- *Diameter*.—Typically 3/16" [4.8 mm.] 1 week before bloom.
- *Length*.—Typically ⅜" [9.5 mm.] 1 week before bloom.
- *Form*.—Not appressed.
- *Surface*.—Pubescent.
- *Tip color*.—White [263. White].

Flowers: Perfect, complete, perigynous, usually a single pistil, about thirty stamens, five sepals and petal locations alternately positioned.

- *Average flower diameter*.—⅞" [22.2 mm.].
- *Number of petals*.—Five, no double blossoms observed.
- *Petal shape*.—Oval to circular.
- *Petal margin*.—Entire, slightly wavy.
- *Average petal diameter*.—7/16" [11.1 mm.].
- *Average petal length*.—½" [12.7 mm.].
- *Petal apex*.—Rounded.
- *Petal base*.—Obtuse.
- *Petal color*.—White [263. White] on both sides.
- *Anther color*.—Moderate orange [53. m.O] over a Light yellow [86. l.Y] center.
- *Stigma color*.—Light greenish yellow [101. l.gY].

*Sepal color*.—A Vivid greenish yellow [97. v.gY] and Grayish yellowish pink [32. gy.yPk] two-tone on the outer surface.
*Sepal length*.—3/16" [4.8 mm.].
*Sepal width*.—5/32" [4.0 mm.].
*Sepal apex*.—Rounded to elliptical to match the width and length.
*Sepal margin*.—Fairly smooth to the naked eye, slightly serrated when magnified.
*Average pistil length*.—11/16" [17.5 mm.].
*Average stamen length*.—7/16" [11.1 mm.].
*Fragrance*.—Moderate.
*Pollen production*.—Moderate, average bee enticement.
*Blooming period*.—Medium, two days before 'September Yummy®' plum (U.S. Plant Pat. No. 14,220).
*Onset of bloom*.—One percent on Feb. 24, 2013.
*Date of full bloom*.—Mar. 6, 2011.
*Duration of bloom*.—One to two weeks, dependent on ambient temperature.
*Bloom density*.—Moderate.
*Number per cluster*.—2 to 8, mostly 3.

Fruit

Maturity when described: Full shipping ripe, Aug. 3, 2013.
Date of first picking: Jul. 27, 2013.
Date of last picking: Aug. 7, 2013.
Size: Uniform, Large.
*Average diameter axially*.—2⅜" [60.3 mm.].
*Average diameter across cheek plane*.—2¾" [69.9 mm.].
*Average diameter across suture plane*.—2⅞" [73 mm.].
*Typical weight*.—7 ounces [198 grams].
Form: Uniform, symmetrical, oblate.
*Longitudinal section form*.—Oblate.
*Transverse section through diameter*.—Round to slightly elliptical.
Suture: An inconspicuous shallow groove extending from the base to just beyond the pistil point.
Ventral surface: Rounded strongly, lipped slightly toward the base and apex on both sides.
Lips: Equal.
Cavity: Flaring, slightly elongated in suture plane, suture showing on one side.
*Depth*.—⅜" [9.5 mm.].
*Breadth*.—1 1/16" [27 mm.].
Base: Truncate, cordate if viewed parallel to the suture.
Apex: Truncate, slightly cordate if viewed parallel to the suture.
Pistil point: An inconspicuous Light brownish gray [63. l.brGy] dot depressed within the suture.
Stem: Medium.
*Average length*.—5/16" [7.9 mm.].
*Average width*.—3/32" [2.4 mm.].
Skin:
*Thickness*.—Medium.
*Surface*.—Smooth.
*Tenacity*.—Tenacious to the flesh.
*Astringency*.—Nonastringent.
*Tendency to crack*.—None observed in dry season.
*Color*.—Black [267. Black] with minor Light brownish gray [63. l.brGy] freckling throughout.
*Bloom*.—Abundant.
Flesh:
*Color*.—Light yellow [86. l.Y] throughout with no observance of internal browning.
*Surface of pit cavity*.—Covered with Grayish yellow [90. gy.Y] broken fibers when twisted away from stone.
*Amygdalin*.—Moderate.
*Juice*.—Abundant, rich.
*Texture*.—Firm, tough, meaty.
*Fibers*.—Abundant, fine.
*Ripens*.—Slightly earliest toward the apex.
*Flavor*.—A tasty blend of acid and sugar, typically 18 brix.
*Aroma*.—Slight.
*Eating quality*.—Very good.

Stone

Type: Clingstone.
Form: Oval.
Hilum: Narrow, oblong.
Base: Rounded with some notched at the hilum.
Apex: Rounded to acuminate with a very sharp 3/32" [2.4 mm.] tip protruding.
Sides: Equal.
Surface: Rough throughout.
External color of stone: Strong yellowish brown [74. s.yBr] when first removed.
Pit wall color when cracked: Moderate yellowish brown [77. m.yBr].
Cavity surface color: Deep brown [56. deep Br].
Average pit wall thickness: 1/16" [1.6 mm.].
Average width: ⅝" [15.9 mm.].
Average length: ⅞" [22.2 mm.].
Average breadth: ⅜" [9.5 mm.].
Tendency to split: Very slight.
Kernel:
*Form*.—Oval.
*Skin color*.—Dark orange yellow [72. d.OY].
*Pellicle color*.—Grayish brown [61. gy.Br].
*Vein color*.—Moderate brown [58. m.Br].
*Taste*.—Slightly bitter.
*Viable*.—Yes.
*Average width*.—⅜" [9.5 mm.].
*Average length*.—9/16" [14.3 mm.].
*Amygdalin*.—Slight.

Use

Market: Fresh market and long distance shipping.
Keeping quality: Good, fruit quality observed to remain in good condition and preserved coloration after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is most similar to 'Plumgiant I' plum tree (U.S. Plant Pat. No. 18,705) by being self-unfruitful and by producing fruit that is clingstone in type, entirely black in skin color, good in flavor, and that matures in the mid to late season, but is distinguished therefrom by producing fruit that is slightly smaller in size, that is oblate in shape instead of globose, that is orange yellow in flesh color instead of white, and that is less prone to internal browning.

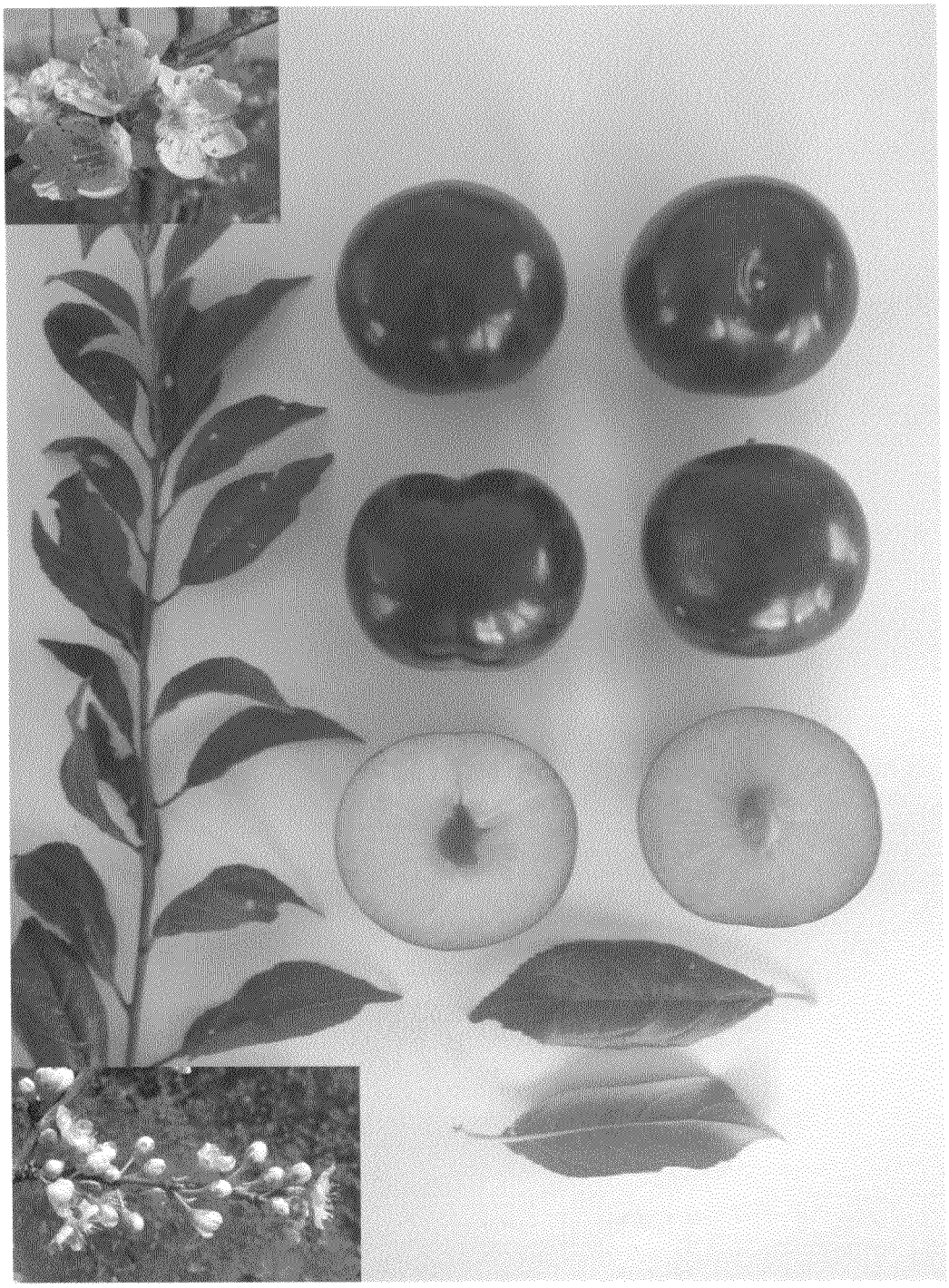

* * * * *